US00PP27333P2

(12) United States Plant Patent
Sanders

(10) Patent No.: US PP27,333 P2
(45) Date of Patent: Nov. 1, 2016

(54) ***DASIPHORA* PLANT NAMED 'LISSDAN'**

(50) Latin Name: ***Dasiphora fruticosa* subsp. *fruiticosa***
Varietal Denomination: LISSDAN

(71) Applicant: Chris Sanders, Eccleshall (GB)

(72) Inventor: Chris Sanders, Eccleshall (GB)

( * ) Notice: Subject to any disclaimer, the term of this patent is extended or adjusted under 35 U.S.C. 154(b) by 162 days.

(21) Appl. No.: 14/120,947

(22) Filed: Jul. 14, 2014

(51) Int. Cl.
*A01H 5/02* (2006.01)

(52) U.S. Cl.
USPC ..... Plt./237

(58) Field of Classification Search
USPC ..... Plt./226, 237
See application file for complete search history.

(56) References Cited

PUBLICATIONS

CPVO 2012, p. 48.*

* cited by examiner

*Primary Examiner* — Keith Robinson
(74) *Attorney, Agent, or Firm* — Penny J. Aguirre

(57) ABSTRACT

A new cultivar of *Dasiphora*, 'LISSDAN', that is characterized by its upright, bushy plant form, its single flowers with the upper surface of the petals bright cerise to fuchsia pink in color and the lower surface of the petals pale cream to parchment in color, and its flowers that retain their color throughout the blooming season.

3 Drawing Sheets

Botanical classification: *Dasiphora fruticosa* subsp. *fruiticosa.*

Variety denomination: 'LISSDAN'

BACKGROUND OF THE INVENTION

The present invention relates to a new and distinct cultivar of *Dasiphora fruticosa* subsp. *fruiticosa* (syn. *Potentilla fruticosa*). The new cultivar will be referred to hereafter by its cultivar name, 'LISSDAN'. 'LISSDAN' is a new cultivar of deciduous shrub grown for landscape use.

'LISSDAN' was discovered by the Inventor as a chance seedling in his garden in Eccleshall, Stafford, United Kingdom in 2007. The parentage is unknown.

Asexual propagation of the new cultivar was first accomplished by softwood cuttings under the direction of the Inventor in Greatham, Hampshire, The United Kingdom in spring of 2008. Asexual propagation by softwood cuttings has determined that the characteristics of the new cultivar are stable and reproduced true to type in successive generations.

SUMMARY OF THE INVENTION

The following traits have been repeatedly observed and represent the characteristics of the new shrub rose. These attributes in combination distinguish 'LISSDAN' as a unique cultivar of *Dasiphora.*

1. 'LISSDAN' exhibits an upright and bushy plant habit.
2. 'LISSDAN' exhibits single flowers with the upper surface of the petals bright cerise to fuchsia pink in color and the lower surface of the petals pale cream to parchment in color.
3. 'LISSDAN' is exhibits flowers that retain their coloration late in the blooming season.

'LISSDAN' can be most closely compared to the *Dasiphora* cultivars 'Marrob' (not patented) and 'Red Ace' (U.S. Plant Pat. No. 4,226). 'Marrob' differs from 'LISSDAN' in having an irregular, lax and less upright plant habit, in having flowers with petals that are orange-red in color and fade to a dull orange on the upper surface and pale green to beige in color on the lower surface. 'Red Ace' differs from 'LISSDAN' in having a less upright and lax plant habit, in having flowers with petals that are less pink in color and fade to a dull orange on the upper surface and pale green to beige in color on the lower surface.

BRIEF DESCRIPTION OF THE DRAWINGS

The accompanying colored photographs illustrate the overall appearance and distinct characteristics of the new *Dasiphora*, 'LISSDAN'.

The photograph in FIG. 1 was taken of a two year-old plant as grown outdoors in the ground in Greatham, Hampshire, United Kingdom.

The photographs in FIG. 2, FIG. 3, FIG. 4, and FIG. 5 were taken of two year-old plants as grown in five-liter containers in Greatham, Hampshire, United Kingdom.

Figure 1:
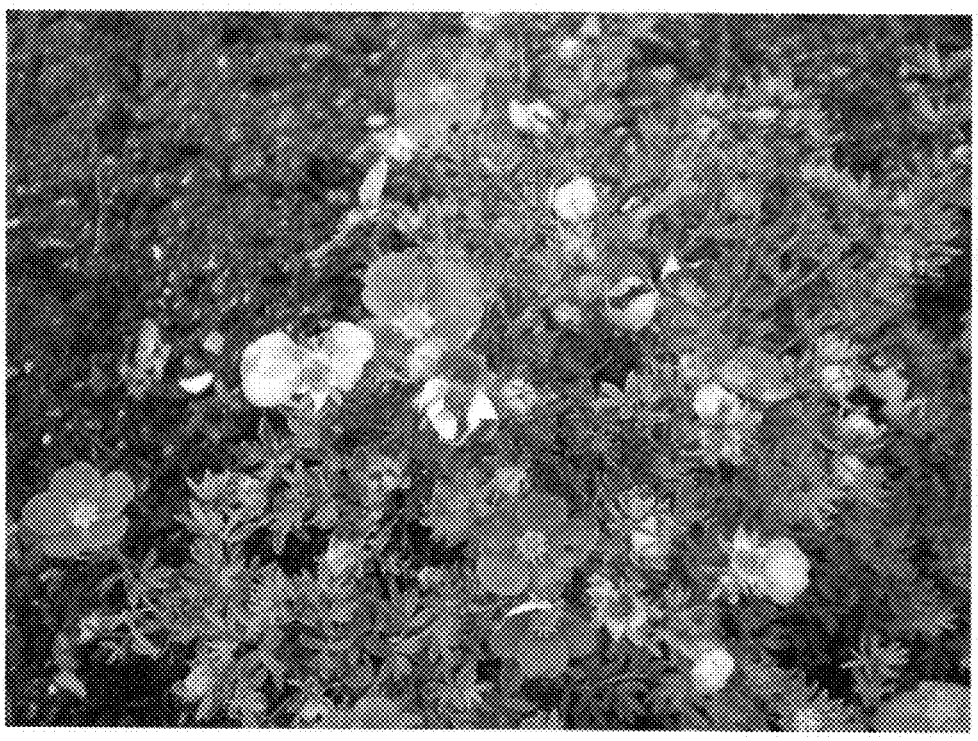

The photograph in FIG. 1 provides a view of 'LISSDAN' in the landscape.

Figure 2:
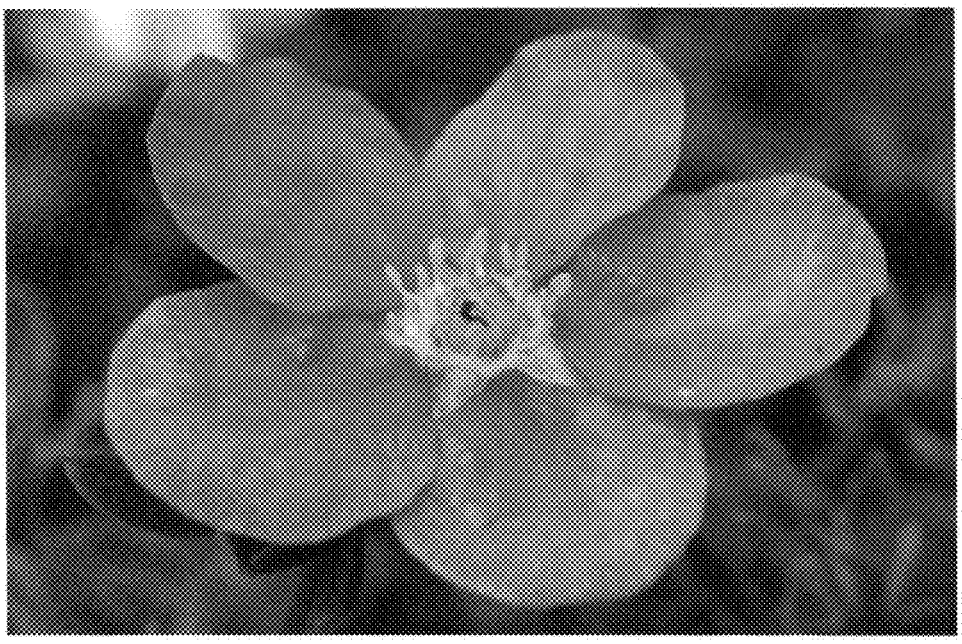

The photograph in FIG. 2 provides a view of a mature flower of 'LISSDAN' in June.

Figure 3:
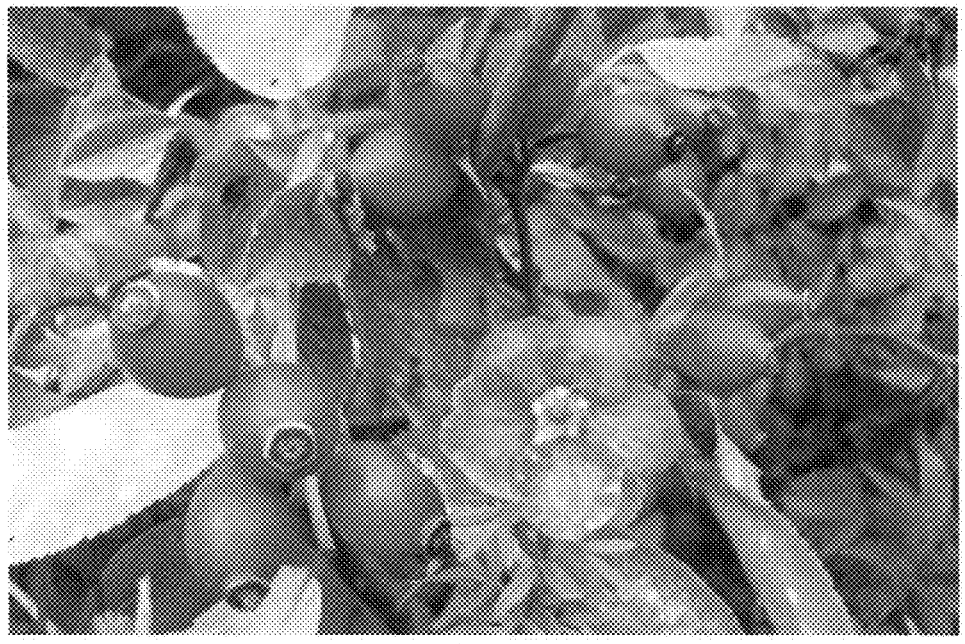

The photograph in FIG. 3 provides a view of the late season flowers and achenes of 'LISSDAN' in September.

Figure 4:
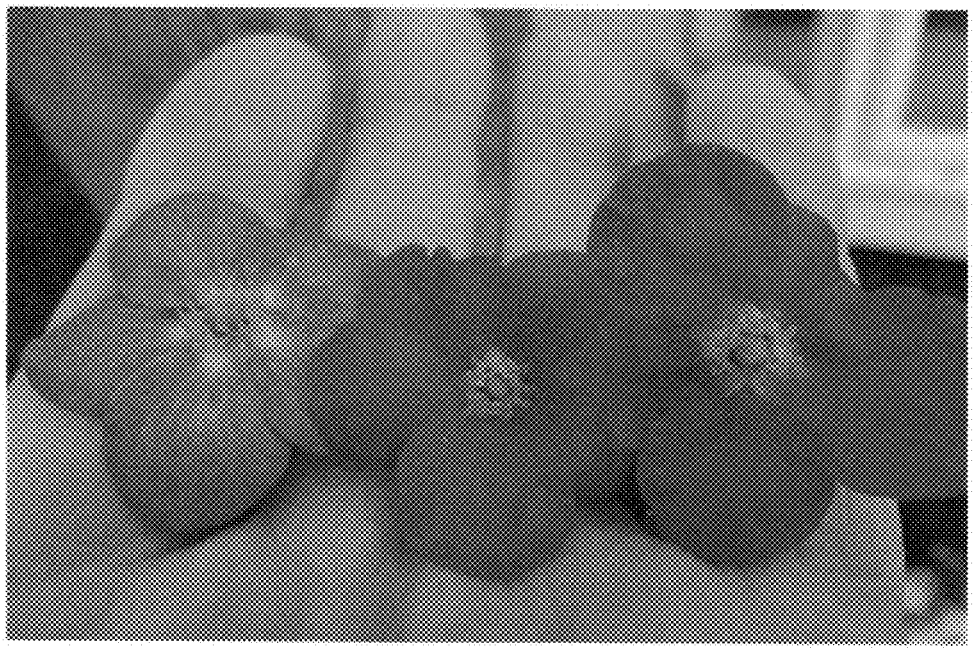

The photograph in FIG. 4 provides a comparison of mature flowers of 'Marrob' on the left, 'LISSDAN' in the center, and 'Red Ace' on the right.

Figure 5:
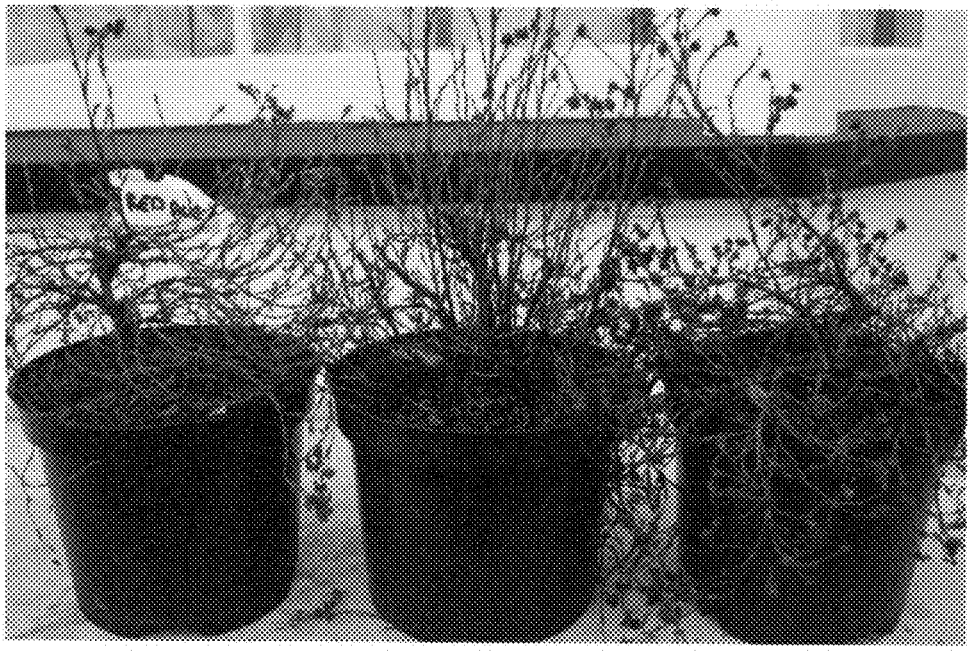

The photograph in FIG. 5 provides a comparison of the winter plant habits of 'Red Ace' on the left, 'LISSDAN' in the center, and 'Marrob' on the right.

The colors in the photographs are as close as possible with digital photography techniques available and the color values cited in the detailed botanical description accurately describe the colors of the new *Dasiphora*.

DETAILED BOTANICAL DESCRIPTION

The following is a detailed description of two year-old plants of the new cultivar as grown outdoors in five-liter containers in Greatham, Hampshire, The United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit*.—From May to mid-September in Liss, Hampshire, The United Kingdom.

*Plant type*.—Deciduous shrub.

*Plant habit*.—Upright and bushy.

*Height and spread*.—An average of 90 cm in height and 35 cm in width in 4 years in the landscape.

*Cold hardiness*.—At least to U.S.D.A. Zone 5.

*Diseases and pests*.—No particular susceptibility and resistance to diseases and pests have been observed.

*Propagation*.—Softwood cuttings.

*Root description*.—Fibrous.

*Growth rate*.—Moderate.

*Time to initiate roots*.—Approximately 14 days.

*Time to produce a rooted young plant*.—Approximately 40 days.

Branch description:

*Branch shape*.—Rounded.

*Branch color*.—Young; 193B, mature wood; 200C.

*Branch surface texture*.—Pubescent, rough and woody with age.

*Branching*.—Freely branching, regular, upright, medium strength.

*Branch size*.—An average of 18 cm in length and 2 mm in diameter (in a 5-liter container).

*Branch quantity*.—An average of 50 lateral branches.

*Internode length*.—Average of 1 cm.

Foliage description:

*Leaves*.—Compound, odd-pinnate division, alternate arrangement, triangular in shape, an average of 14.5 cm in length and 23.5 cm in width, internodes; an average of 10.5 cm in length.

*Leaflets*.—5, narrow elliptic in shape, acute apex, cuneate base, entire margins, color 138A on upper surface and 138C on lower surface, glabrous upper surface, pubescent lower surface, veins; pinnate and inconspicuous, terminal leaflet an average of 9.5 mm in length and 4 mm in width, central leaflets; an average of 10.5 mm in length and 2.5 mm in width, basal leaflets; an average of 11 mm in length and 2.5 mm in width.

*Stipules*.—Elliptic to lanceolate in shape, an average of 6 mm in length and 2.5 mm in width, color upper and lower surface; 166A, upper and lower surface slightly pubescent.

*Petioles and petiolules*.—Petioles; an average of 2.5 cm in length and 3 mm in diameter, petiolules; an average of 1 cm in length and 2 mm in diameter, petioles and petiolules; color 193B, surface texture glabrous.

Inflorescence description:

*Inflorescence type*.—Solitary, axillary at the apex of stems.

*Flower number*.—An average of 2 to 3 per main stem.

*Flower fragrance*.—None.

*Flower longevity*.—About 5 days, self-cleaning.

*Flower type*.—Single.

*Flower aspect*.—Upwards at an average angle of 45° from horizontal.

*Flower size*.—An average of 2 cm in diameter and 8 mm in depth.

*Peduncles*.—An average of 2 mm in length and 1 mm in diameter, pubescent surface, 143C to 143D in color, medium strength.

*Pedicels*.—An average of 10 mm in length, 1 mm in diameter, pubescent surface, 138D in color, medium strength.

*Flower buds*.—Flattened globose in shape, an average of 5 cm in length and 8 cm in diameter prior to opening, 11C in color.

*Sepals*.—5, ovate in shape, entire margin, color on upper and lowers surface; base, 150D and tip 181B, an average of 6 mm in length and 4 mm in width, acuminate apex, truncate base, slightly pubescent on upper and lower surface, epicalyx; 5-lobed, lanceolate in shape, entire margin, acute apex, an average of 4 mm in length and 2 mm in width, upper and lower surface; 138C in color and very slightly pubescent.

*Petals*.—An average of 5 per flower, self-cleaning, oval-rounded in shape, smooth upper and lower surface, margin entire, slightly undulate and notched, cuneate base, rounded apex, an average of 11 mm in length and 14 mm in width, color when fully open; N57A to N57B on upper surface and 3D on lower surface, color when fading; N57C to N57D on upper surface and 4D on lower surface.

*Receptacle*.—Pubescent, 7 mm in width, 3 mm in depth, N144B in color.

*Pistils*.—About 60, 1.5 mm in length, stigma capitate in shape, an average of 0.5 mm in diameter and 164A in color, style is an average of 1 mm in length and 0.5 mm in width, 14D in color, ovary is superior and 1D in color.

*Stamens*.—30 to 35 per flower, filaments are an average of 1.25 mm in length and 14C in color, anthers are an average of 1 mm in length, an average of 0.5 mm in width, flattened ovoid in shape and 14B in color, pollen is minimal in quantity and 14C in color.

*Achenes*.—Oval in shape, an average of 2 cm in length and 1 cm in width, N57A in color with apex N200B, satiny surface.

*Seed*.—Very sparse in quantity, an average of 1 mm in length and 0.5 mm in width, a blend between 199A to 200D in color.

It is claimed:

1. A new and distinct cultivar of *Dasiphora* plant named 'LISSDAN' as herein illustrated and described.

* * * * *